US008835175B2

(12) United States Patent
Diez Cervantes et al.

(10) Patent No.: US 8,835,175 B2
(45) Date of Patent: Sep. 16, 2014

(54) CULTURE MEDIUM FOR HUMAN MESENCHYMAL STEM CELLS

(71) Applicant: Grifols, S.A., Barcelona (ES)

(72) Inventors: Jose Maria Diez Cervantes, Barcelona (ES); Rodrigo Gajardo Rodriguez, Barcelona (ES)

(73) Assignee: Grifols, S.A., Barcelona (ES)

( * ) Notice: Subject to any disclaimer, the term of this patent is extended or adjusted under 35 U.S.C. 154(b) by 0 days.

(21) Appl. No.: 13/833,545

(22) Filed: Mar. 15, 2013

(65) Prior Publication Data

US 2014/0134724 A1 May 15, 2014

(30) Foreign Application Priority Data

Nov. 13, 2012 (ES) .................................. 201231753

(51) Int. Cl.
*C12N 5/077* (2010.01)

(52) U.S. Cl.
USPC .......................................................... 435/405

(58) Field of Classification Search
USPC .......................................................... 435/405
See application file for complete search history.

(56) References Cited

U.S. PATENT DOCUMENTS

2005/0260748 A1* 11/2005 Chang et al. .................. 435/366

FOREIGN PATENT DOCUMENTS

| | | | |
|---|---|---|---|
| EP | 2 233 565 | A1 | 9/2010 |
| EP | 2 545 928 | A1 | 1/2013 |
| WO | WO 2007/044418 | A2 | 4/2007 |
| WO | WO 2007/149328 | A1 | 12/2007 |

OTHER PUBLICATIONS

Capelli et al., "Human platelet lysate allows expansion and clinical grade production of mesenchymal stromal cells from small samples of bone marrow aspirates or marrow filter washouts," Bone Marrow Transplant 40:785-791, 2007.*

T. Cartwright, et al., "Culture media", Basic cell culture, 2$^{nd}$ edition, Davis, J.M. ed. 2002. Oxford University Press, New York, USA.

J. Sato, et al., "Specific cell types and their requirements", Basic cell culture, 2$^{nd}$ edition, Davis, J.M. ed. 2002, Oxford University Press, New York, USA.

Van Der Valk J. et al.: "Optimization of chemically defined cell culture mdia Replacing fetal bovine serum in mammalian in vitro methods", Toxicology in vitro, Elsevier Science, GB, vol. 24, No. 4, Jun. 1, 2010, pp. 1053-1063, XP027048454, ISSN: 0887-2333.

Capelli C. et al.: "Human platelet lysate allows expansion and clinical grae production of mesenchymal stromal cells from small samples of bone marrow aspirates or marrow filter washouts", Bone Marrow Transplantation, Nature Publishing Group, GB, vol. 40, No. 8, Oct. 1, 2007, pp. 785-791, XP002545732, ISSN:0268-3369.

Doucet Christelle et al.: "Platelet lysates promote mesenchymal stem cell expansion: A safety substitute for animal serum in cell-based therapy application", Journal of Cellular Physiology, Wiley Subscription Services, Inc., vol. 205, No. 2, Nov. 1, 2005, pp. 228-236, XP002454867, ISSN:0021-9541.

Sunghoon Jung et al.: "ex Vivo Expansion of Human Mesenchymal Stem Cells in Defined Serum-Free Media", Stem Cells International, vol. 42, No. 8-9, Jan. 1, 2012, pp. 235-21, XP055060981, ISSN:1687-966X.

Bieback Karen et al.: "Human alternatives to fetal bovine serum for the expansion of mesenchymal and embryonic stromal cells from bone marrow", Stem Cells, Alphamed Press, Inc, United States, vol. 27, No. 9, Sep. 1, 2009, pp. 2331-2341, XP001525902, ISSN:1549-4918.

Mannello F. et al.: "Concise review: No breakthroughs for human mesenchymal and embryonic stem cell culture: Conditioned medium, feeder layer, or feeder-free; medium with fatal calf serum, human serum replacement nonconditioned medium, or ad hoc formula? All that glitters is not go", Stem Cells, Alphamed Press Dayton, OH, US, vol. 25, No. 7, Jan. 1, 2007, pp. 1603-1609, XP002466979, ISSN:1066-5099.

Muller I et al.: "Animal serum-free culture conditions for isolation and expansion of multipotent mesenchymal stroma cells from human BM", Cytotherapy, Isis Medical Media, Oxford, GB, vol. 8, No. 5, Jan. 1, 2006, pp. 437-444, XP008127344, ISSN:1465-3249.

European search report dated Jul. 5, 2013 in corresponding EP Application No. 13160782.2 filed Apr. 9, 2013.

* cited by examiner

*Primary Examiner* — Rosanne Kosson
(74) *Attorney, Agent, or Firm* — RatnerPrestia

(57) ABSTRACT

A culture medium for human mesenchymal stem cells (hMSC) includes a mesenchymal stem cell basal medium; human leucocyte/platelet coat lysate; insulin; sodium selenite; ethanolamine; and basic fibroblast growth factor. This culture medium is effective for growing hMSC lines, including those which do not grow in culture medium normally used for this type of cell.

13 Claims, No Drawings

CULTURE MEDIUM FOR HUMAN MESENCHYMAL STEM CELLS

FIELD OF THE INVENTION

This invention relates to a new culture medium for human mesenchymal stem cells (hMSC). More particularly this invention relates to a culture medium in which hMSC lines can grow, including those which do not grow in the culture media normally used for cells of this type because they have adapted to specific culture media.

BACKGROUND OF THE INVENTION hMSC are multipotent cells fundamentally characterised by their ability to differentiate into various mesenchymal tissues such as bone, cartilage, tendon, muscle and adipose tissue, among others. hMSC can be isolated from various tissues in adults, including those which are to be found in bone marrow, adipose tissue and the blood of the umbilical cord.

The anti-proliferative, immunomodulating and anti-inflammatory effect of hMSC has centred attention on these cells as potential therapeutic agents in diseases caused by the immune system, including graft versus host diseases, rejection following the transplant of solid organs and autoimmune diseases.

It is known that for the in vitro culture of hMSC it is imperative to preserve their pluripotential capacity, and for this the addition of exogenous factors such as for example basic fibroblast growth factors (bFGF), epidermal growth factor (EGF) and transforming growth factor (TGFβ-1) to a normal culture media is required. However most hMSC are dependent on a specific culture medium and also cannot be cultured on the media which have been conventionally used for the culture of mesenchymal stem cells such as DMEM/F12 medium supplemented with bovine foetal serum qualified for mesenchymal stem cells (MSCQ).

SUMMARY OF THE INVENTION

In order to overcome these problems this invention relates to a novel culture medium for hMSC on which hMSC that do not grow in other culture medium formulations can grow. The culture medium according to this invention comprises:

a) Basal medium normally used for the culture of mesenchymal stem cells
b) human leucocyte/platelet coat lysate (buffy coat; LBC)
c) insulin
d) sodium selenite
e) ethanolamine
f) basic fibroblast growth factor (bFGF)

DETAILED DESCRIPTION OF THE INVENTION

As used in this document the term "culture medium" relates to a nutrient solution for the culturing, growth or proliferation of cells. The term "cell culture" refers to cells which are maintained, cultivated or grown in an artificial in vitro environment.

The term "basal media" or "basal medium" used in this document refers to any medium in which human mesenchymal cells are capable of growing when supplemented with different supplements, which may or may not contain serum. Basal media provide standard inorganic salts such as zinc, iron, magnesium, calcium and potassium, together with vitamins, glucose, a buffer system and essential amino acids.

Preferably the basal medium normally used for the culture of mesenchymal cells in the culture medium according to this invention is DMEM/F12+pyruvate, DMEM/F12 medium being a mixture of equal parts of Dubelcco's Modified Eagle Medium (DMEM), which is a modification of the minimum essential medium developed by Harry Eagle, and Ham's F12 medium, developed by Ham for the growth of CHO (Chinese Hamster Ovary) cells, Ham's F10, Ham's F12, MCDB 131, a medium developed by Knedler and Ham as a medium with reduced serum supplement for the growth of human cells, or RPMI 1640, the name of which derives from the initials of the Roswell Park Memorial Institute where it was developed by Moore and co-workers for the culture of normal and neoplastic lymphocytes, although when adequately supplemented it can grow other different types of cells. The formulation and composition of these media is widely known and can be obtained from any producer or supplier, such as for example Gibco (Life Technologies). More preferably the medium is DMEM/F12+pyruvate.

One of the components of the culture medium for human mesenchymal cells according to this invention is leucocyte/platelet coat lysate. The leucocyte/platelet coat, also known as "buffy coat", is the coat which is observed between the plasma and the red cells after the centrifuging or sedimentation of whole blood. It basically comprises leucocytes and platelets. The leucocyte/platelet coat lysate (buffy coat) is present in the culture medium according to this invention in a quantity of between 5 and 20% (v/v), more preferably between 7 and 15% (v/v), and most preferably 10% (v/v).

Another of the components of the culture medium according to this invention is insulin. The beneficial effect of insulin on cell growth is known (Cartwright, T. y Shah, G. P culture media. Basic cell culture, 2nd edition, Davis, J. M. ed. 2002. Oxford University Press, New York, USA). In the culture medium according to this invention insulin is preferably present in a quantity of between 2 and 20 mg/L, more preferably between 5 and 15 mg/L and most preferably 10 mg/L.

Also another component of the culture medium according to this invention is selenium in the form of sodium selenite. Selenium is a trace element which is normally provided to culture medium by serum and which may be essential for it. Sodium selenite is present in the culture medium in a quantity of between 0.005 and 1.730 mg/L.

Furthermore the culture medium for human mesenchymal cells according to this invention comprises ethanolamine. It is known that ethanolamine encourages the construction of cell membranes. The ethanolamine in the culture medium according to this invention is present in a quantity of between 1 and 8 mg/L, preferably between 2 and 5 mg/L.

Finally the culture medium for mesenchymal cells according to this invention also comprises bFGF. It is known that bFGF has been recommended for culturing mesenchymal cells (Sato, J. et al. Specific cell types and their requirements. Basic cell culture, 2nd edition, Davis, J. M. ed. 2002. Oxford University Press, New York, USA). The bFGF is present in the culture medium according to this invention in a quantity of between 5 and 25 ng/mL.

Surprisingly, with the combination of components in the culture medium according to this invention it is possible to cultivate human mesenchymal cell lines, including those adapted to other culture media that are generally commercially available, which do not grow in the culture media normally used for this type of cells, such as for example the human mesenchymal cells offered by Lonza or PromoCell.

Optionally the culture medium according to this invention comprises an antibiotic. Any antibiotic normally used in the culturing of this type of cells may be used. Preferably this antibiotic is a mixture of gentamycin amphotericin. The quantity of antibiotic that has to be used in the culture medium may easily be determined by a person skilled in the art.

For the growth of mesenchymal stem cells it is essential that the culture medium according to this invention be supplemented, for example by foetal bovine serum (FBS) or cell culture supplement derived from human plasma (CCS), obtained, for example, as described in U.S. Pat. No. 8,252,590 B2. If FBS is used, a quantity of between 10 and 20% (v/v) is considered to be sufficient. On the other hand if CCS is used to supplement the culture medium according to this invention, a quantity of between 10 and 40% (v/v) may be considered sufficient.

The culture medium for human mesenchymal stem cells according to this invention may be in dry form or in liquid form. For use in dry form its components may be dissolved in a suitable liquid for the culture of mesenchymal cells. The type of liquid in which the components of the culture medium according to this invention may be dissolved is known to those skilled in the art, such as for example sterile distilled water.

This invention is described in further detail below with reference to a number of embodiments. These examples are however not intended to limit the scope of this invention.

EXAMPLES

Example 1

A culture medium according to this invention containing DMEM/F12+pyruvate as basal medium, 10% (v/v) human leucocyte/platelet coat lysate (buffy coat), 10 mg/L of insulin, 0.0067 mg/L of sodium selenite, 2 mg/L of ethanolamine and 20 ng/mL of bFGF was prepared. This medium was referred to as LV2. Medium LV2 was used alone or supplemented with 10% (v/v) of foetal bovine serum (FBS) qualified for mesenchymal stem cells (MSCQ) or with 15% (v/v) of cell culture supplement derived from human plasma (CCS). hMSC commercially available from Lonza (Basel, Switzerland) or PromoCell (Heidelberg, Germany) were cultured. The culture media recommended by the manufacturer were used as a positive control. Just one commercially available basal medium was used as the negative control. The results are shown in Table 1.

TABLE 1

Experimental results from the culturing of Lonza and PromoCell hMSC.

| | Cell Growth | |
|---|---|---|
| Culture Medium | Lonza hMSC | PromoCell hMSC |
| Recommended by the manufacturer | (+) | (+) |
| DMEM/F12 | (−) | (−) |
| DMEM/F12 + FBS (MSCQ) | (−) | (−) |
| DMEM/F12 + CCS | (−) | (−) |
| LV2 | (−) | (−) |
| LV2 + FBS (MSCQ) | (+) | (+) |
| LV2 + CCS | (+) | (+) |

As may be seen in Table 1, Lonza hMSC are no longer able to grow when only DMEM/12 basal medium is used as the culture medium, including when that basal medium is supplemented with FBS or CCS. They also do not grow when LV2 medium according to this invention is used alone. However they were capable of growing in the culture medium according to this invention when it was supplemented with FBS or CCS, and in the culture medium recommended by the manufacturer.

Example 2

In order to determine the effect of combining all the components of the culture medium according to this invention an LV2 culture medium was prepared as described in Example 1 and in addition to this various media which lacked at least one component of the culture medium according to this invention were also prepared. The media prepared, and the results obtained, are shown in Table 2.

TABLE 2

Effect of leaving out components from the culture medium on the growth of Lonza and PromoCell hMSC.

| | Cell growth | |
|---|---|---|
| Culture medium | Lonza hMSC | PromoCell hMSC |
| Recommended by the manufacturer | (+) | (+) |
| DMEM/F12 | (−) | (−) |
| LV2 + CCS | (+) | (+) |
| LV2 + CCS without insulin, sodium selenite and ethanolamine | (−) | (−) |
| LV2 + CCS without leucocyte/platelet lysate(buffy coat) | (−) | (−) |
| LV2 + CCS without bFGF | (−) | (−) |
| LV2 + CCS without LBC/bFGF | (−) | (−) |

As may be seen from Table 2, Lonza and PromoCell hMSC only grew in the culture medium recommended by the manufacturer and in the culture medium according to this invention supplemented with CCS. When at least one of the components of the culture medium according to this invention was left out the hMSC were no longer capable of growing in it.

Although the invention has been described in relation to examples of preferred embodiments, these must not be regarded as restricting the invention, which is defined by the broadest interpretation of the following claims.

The invention claimed is:

1. A culture medium for human mesenchymal stem cells, comprising:
 a) mesenchymal stem cell basal medium;
 b) human leucocyte and platelet coat (buffy coat) lysate;
 c) insulin;
 d) sodium selenite;
 e) ethanolamine; and
 f) basic fibroblast growth factor (bFGF).

2. The culture medium for human mesenchymal cells according to claim 1, wherein the mesenchymal stem cell basal medium is DMEM/F12+pyruvate, Ham's F10, Ham's F12, MCDB 131 or RPMI 1640.

3. The culture medium for human mesenchymal stem cells according to claim 2, wherein the human leucocyte and platelet coat (buffy coat) lysate is present in the culture medium in a quantity of 5 to 20% (v/v).

4. The culture medium for human mesenchymal stem cells according to claim 2, wherein the human leucocyte and platelet coat (buffy coat) lysate is present in the culture medium in a quantity of 7 to 15% (v/v).

5. The culture medium for human mesenchymal cells according to claim 4, wherein the insulin is present in a quantity of 2 to 20 mg/L.

6. The culture medium for human mesenchymal cells according to claim 5, wherein the insulin is present in a quantity of 5 to 15 mg/L.

7. The culture medium for human mesenchymal cells according to claim 6, wherein the sodium selenite is present in a quantity of 0.005 to 1.730 mg/L.

8. The culture medium for human mesenchymal cells according to claim 7, wherein the ethanolamine is present in a quantity of 1 to 8 mg/L.

9. The culture medium for human mesenchymal stem cells according to claim 8, wherein the ethanolamine is present in a quantity of 2 to 5 mg/L.

10. The culture medium for human mesenchymal cells according to claim 9, wherein the bFGF is present in a quantity of 5 to 25 ng/mL.

11. The culture medium for human mesenchymal cells according to claim 10, further comprising an antibiotic.

12. The culture medium for human mesenchymal stem cells according to claim 11, wherein the antibiotic is a mixture of gentamycin and amphotericin.

13. The culture medium for human mesenchymal cells according to claim 12, wherein said medium is supplemented with foetal bovine serum (FBS) in a quantity of 10% to 20% (v/v).

* * * * *